Figure 1:
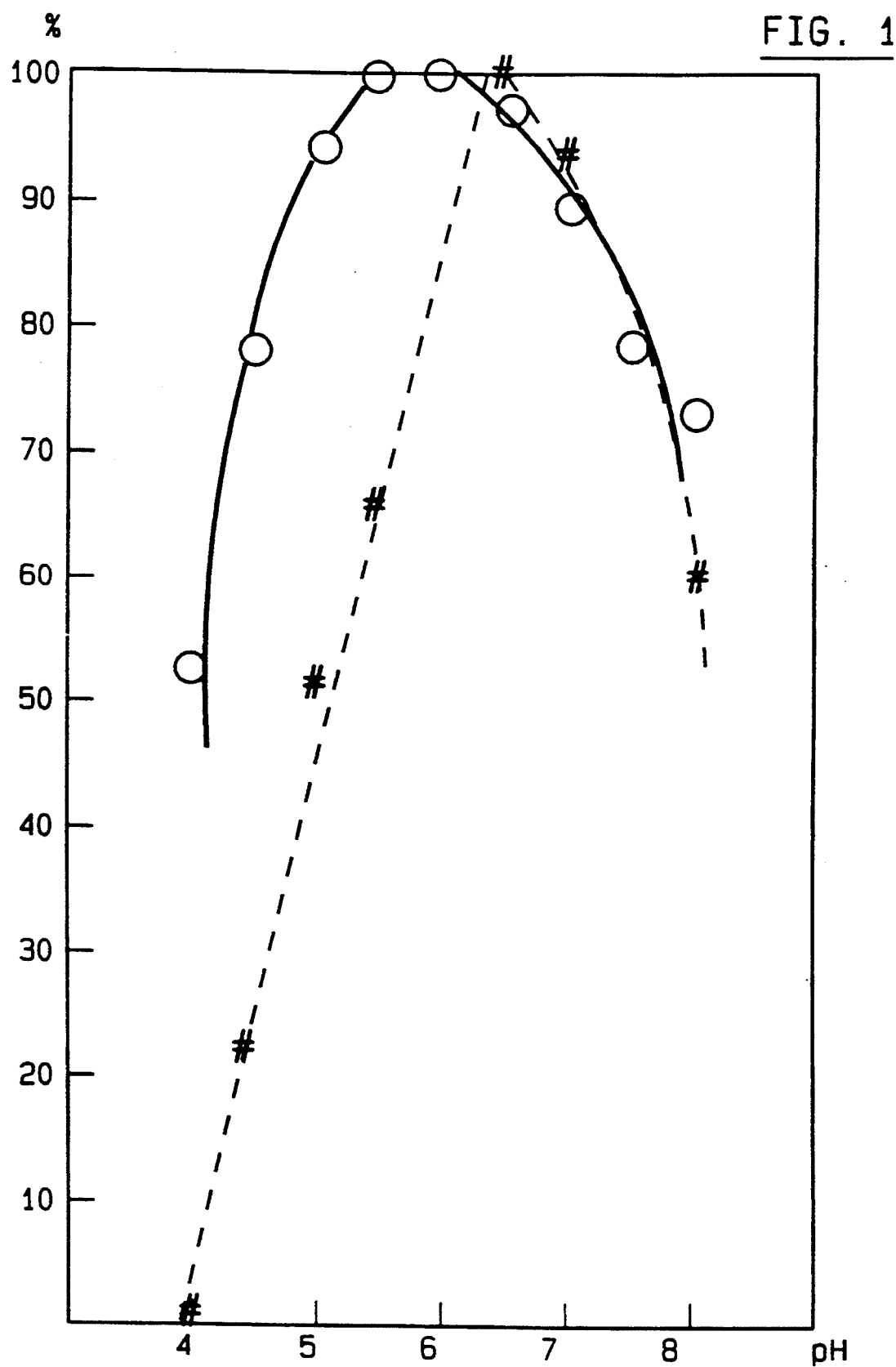

United States Patent [19]

Charles et al.

[11] Patent Number: 5,334,524

[45] Date of Patent: Aug. 2, 1994

[54] **PROCESS FOR PRODUCING LEVAN SUCRASE USING *BACILLUS LICHENIFORMIS***

[75] Inventors: Robert L. Charles; Jayarama K. Shetty, both of Elkhart, Ind.

[73] Assignee: Solvay Enzymes, Inc., Houston, Tex.

[21] Appl. No.: 884,183

[22] Filed: May 18, 1992

[51] Int. Cl.$^5$ .................. C12N 9/00; C12N 1/20; C12N 9/10; A61K 37/50

[52] U.S. Cl. .................. 435/193; 435/183; 435/252.5; 435/836; 424/94.5

[58] Field of Search ............ 435/193, 173, 183, 252.5, 435/836; 424/94.5

[56] References Cited

U.S. PATENT DOCUMENTS

| | | | |
|---|---|---|---|
| 4,309,505 | 1/1982 | Smith et al. | 435/193 |
| 4,423,150 | 12/1983 | Heady | 435/193 |
| 4,617,269 | 10/1986 | Rathbone et al. | 435/193 |
| 4,849,356 | 7/1989 | Van Dooren et al. | 435/193 |
| 4,879,228 | 11/1989 | Mays et al. | 435/82 L |
| 5,162,207 | 11/1992 | Nagarajan et al. | 435/69.1 |

FOREIGN PATENT DOCUMENTS

| | | | |
|---|---|---|---|
| 0301628 | 2/1989 | Australia | 435/193 |
| 0307158 | 3/1989 | European Pat. Off. | 435/193 |
| 52-82781 | 7/1977 | Japan . | |
| 3-198773 | 8/1991 | Japan | 435/193 |
| 8403518 | 9/1984 | World Int. Prop. O. | 435/193 |

OTHER PUBLICATIONS

Brobst, K. M. & Schobell, H. B., Starch/Stark, 34, pp. 117–121 (1982).
Amory et al., (1987), Journal of Bacteriology, (169), pp. 324–333.
Caulfield et al., (1979), Journal of Bacteriology, 138, pp. 345–351.
Pascal et al., (1971), Biochimie, 53, pp. 1059–1066.
Dedonder, (1966), Methods of Enzymology, 8, pp. 500–505.

*Primary Examiner*—Douglas W. Robinson
*Assistant Examiner*—Jeffrey J. Seviguy
*Attorney, Agent, or Firm*—Willian Brinks Hofer Gilson & Lione

[57] ABSTRACT

The present invention relates to an acid stable levan sucrase enzyme which is not induced by sucrose.

The present invention relates to a process for the preparation of this enzyme and microorganisms producing the levan sucrase enzyme. The invention also provides compositions containing this enzyme.

11 Claims, 2 Drawing Sheets

PROCESS FOR PRODUCING LEVAN SUCRASE USING BACILLUS LICHENIFORMIS

The present invention relates to an acid stable levan sucrase enzyme, microorganisms producing it, a process for the preparation of this acid stable levan sucrase enzyme and compositions containing it.

Levan sucrase enzymes catalyze the transfer of fructose. More precisely levan sucrase enzymes (E.C.2.4.1.10) catalyze the transfer of fructosyl residues from sucrose, raffinose or stachyose to an appropriate co-substrate, producing polymers, generally called levans, containing varying amounts of fructosyl residues consisting of $\beta 2 \rightarrow 6$ linkages. Levans have widespread applications in the chemical and food industry as well as medicine and research.

Levan sucrase enzymes have been isolated from a variety of microbial sources, microorganisms such as *Acetobacter suboxydans*, *Actinomyces viscosus*, *Aerobacter levanicum*, *Bacillus amyloliquefaciens*, *Bacillus licheniformis*, *Bacillus mesentericus*, *Bacillus subtilis*, *Glucobacter oxydans*, *Streptococcus mutans*, *Streptococcus salivarius*, *Streptomyces griseus*, *Zymomonas mobilis*. In most cases, the enzyme is extracellular and heat labile. One of the most important features in the production of levan sucrase enzymes is that at least 5% sucrose must be added to the growth medium in order to induce the synthesis of the enzyme using known levan sucrase enzymes producing microorganisms.

As a result, it becomes difficult to separate levan sucrase enzyme from the culture broth because the viscosity of the culture broth increases as levan is produced during fermentation. So there is always a constant search for microorganisms requiring low levels or no sucrose for the production of levan sucrase.

Japanese Patent Application JP-A-52-82781 discloses a method for producing an extracellular levan sucrase enzyme in the presence of low concentrations of sucrose (0.3% weight/volume) using *Bacillus licheniformis* strain AJ 3982 (Institute of Microbial Engineering deposition No. 3373). However this enzyme still needs sucrose to be induced and produced. Moreover this levan sucrase enzyme does not develop any enzymatic activity at a pH of 4.0 when held at a temperature of 55° C. At said temperature it develops only 50% of its maximum activity at a pH of about 5.2 and about 80% of its maximum activity at a pH from about 6 to about 7.8. This narrow pH range restricts the field of application of this levan sucrase enzyme. Moreover acid stability of the levan sucrase enzyme is very important for widespread commercial application of the enzyme.

The present invention aims to provide a levan sucrase enzyme, which develops an enzymatic activity in a wider pH range than the known enzymes and which is stable at acid pHs at which known enzymes are not.

For this purpose, the present invention provides an acid stable levan sucrase enzyme derived from a microorganism belonging to the species Bacillus and developing, at a temperature of about 55° C. and at a pH of 4.0, an enzymatic activity of at least 50% of the maximum activity measured at 55° C.

The levan sucrase enzyme according to the invention develops an appreciable enzymatic activity in a wide pH range in the presence of a substrate such as sucrose. It develops at a pH in the range of about 5.5 through about 6.3 a maximum enzymatic activity measured at about 55° C.

More precisely it develops, at a temperature of about 55° C. and at a pH in the range of about 4.0 through about 8.4, an enzymatic activity of at least 50% of the maximum activity measured at 55° C. It develops, at said temperature of about 55° C. and at a pH in the range of about 4.2 through about 8.0, an enzymatic activity of at least 70% of the maximum activity measured at 55° C. It develops, at said temperature and at a pH in the range of about 4.5 through about 7.8, an enzymatic activity of at least 80% of the maximum activity measured at 55° C. It develops, at about 55° C. and at a pH in the range of about 4.7 through about 7.2, an enzymatic activity of at least 90% of the maximum activity measured at 55° C.

The levan sucrase enzyme according to the invention has an appreciable thermal stability in the presence of a substrate such as sucrose. It develops at a temperature in the range of about 55° C. through about 64° C. a maximum enzymatic activity measured at a pH of 5.5.

More precisely it develops, at a pH of about 5.5 and at a temperature in the range of about 35° C. through about 75° C., an enzymatic activity of at least 50% of the maximum activity measured at a pH of 5.5. It develops, at said pH of about 5.5 and at a temperature in the range of about 45° C. through about 68° C., an enzymatic activity of at least 80% of the maximum activity measured at a pH of 5.5. It develops at said pH of about 5.5 and at a temperature in the range of about 50° C. through about 67° C., an enzymatic activity of at least 90% of the maximum activity measured at a pH of 5.5.

The levan sucrase enzyme according to the invention is a cell bound enzyme. It has a fructosyl transferase activity and so is able to produce fructosyl polymers from sucrose consisting of $\beta$-D($2 \rightarrow 6$) linked fructose which belong to the "levan" family.

The levan sucrase enzyme according to the invention is not a sucrose inducible enzyme, i.e. it does not need sucrose to be induced and produced.

The present invention also provides a process for the production of an acid stable levan sucrase enzyme using a microorganism in the absence of added sucrose to the nutrient medium.

The process according to the invention for the production of an acid stable levan sucrase enzyme comprises the following steps of:

(i) cultivating a microorganism belonging to the genus Bacillus in a suitable nutrient medium by forming a fermentation broth comprising a biomass and (ii) recovering the levan sucrase enzyme from said fermentation broth, wherein the microorganism is cultivated in the absence of sucrose.

The present invention also aims to provide a new microorganism belonging to the genus Bacillus producing an acid stable levan sucrase enzyme in the absence of sucrose in the nutrient medium.

For this purpose the present invention provides a new microorganism of the species *Bacillus licheniformis* producing an acid stable levan sucrase enzyme in the absence of sucrose in the nutrient medium. The preferred microorganism of the species *Bacillus licheniformis* has been deposited with the Agricultural Research Culture Collection (NRRL), Peoria, Ill., under the Budapest Treaty.

The deposit number is NRRL B-18962.

Natural and artificial mutants and derivatives obtained by natural modifications or by genetic modifications of the microorganism of the species *Bacillus licheniformis* APMC 84 are also encompassed by the present invention.

The levan sucrase enzyme of the present invention can be produced not only by the strain of *Bacillus licheniformis* APMC 84 B-1896, but also by natural or artificial mutants and other derivatives of this microorganism. Such mutants can be obtained by well-known techniques, such as X-ray, ultraviolet irradiation, chemical mutagens and genetic engineering.

The levan sucrase enzyme produced in accordance with the process of the invention is prepared by cultivating the microorganism belonging to the genus Bacillus in a nutrient medium containing carbon, nitrogen and inorganic salts under aerobic conditions in the absence of sucrose and then recovering the levan sucrase enzyme therefrom.

The conditions of culture of these microorganisms, such as components of the nutrient medium, parameters, temperature, pH, agitation, aeration, are apparent for a man skilled in the art.

Suitable carbon sources include glucose, fructose, maltodextrins, glycerol, corn syrup, starch, hydrolyzed starch or mixtures of two or more of these carbon sources. Preferred carbon sources are corn syrup and hydrolyzed starch.

Nitrogen sources which can be used include soybean flour, corn steep liquor, potato meal, cottonseed meal, fish meal, yeast, yeast extract or mixtures of two or more of these nitrogen sources. Preferred nitrogen sources are soybean flour, cottonseed meal, yeast extract and a mixture of soybean flour and yeast extract.

Suitable salts include potassium sulfate, manganese sulfate, ammonium sulfate, ammonium citrate, potassium phosphate, sodium monohydrogen phosphate, sodium dihydrogen phosphate, calcium chloride, sodium titrate or blends of two or more of these salts. Preferred salts include a blend of sodium monohydrogen phosphate, sodium dihydrogen phosphate, calcium chloride and sodium citrate.

The medium containing the above components is sterilized in a conventional manner and inoculated with the appropriate strain of microorganism, preferably with the strain of *B. licheniformis* and more preferably the strain of *B. licheniformis* NRRL B-18962.

Cultivation is conducted aerobically with shaking or under aerated agitation, typically at a temperature between about 25° and 46° C. for about 6 to 40 hours and at a pH between about 5.0 and about 8.5. Preferably cultivation is conducted at a temperature between about 30° and 42° C. for about 12 to 30 hours and at a pH between about 6.0 and 8.0. Good results are obtained when cultivation is conducted at a temperature between about 36° and 40° C. at a pH between about 6.5 and 8.5.

After the cultivation, a fermentation broth comprising a biomass is obtained. This biomass, comprising the cells of the microorganisms with the cell bound levan sucrase enzyme, is separated and recovered from the culture filtrate using conventional methods such as centrifugation, salting out, precipitation, filtration, ultrafiltration, filtration, microfiltration, centrifugation followed by ultrafiltration or filtration followed by microfiltration.

The separated and recovered biomass is subsequently washed, preferably several times with water, and more preferably with deionized distilled water, and homogenized. Repeated washing of the biomass has no effect on the cell bound levan sucrase enzyme activity leading to the conclusion that the enzyme is tightly bound to the cell.

The levan sucrase enzyme can further be purified if necessary and according to the planned uses. Solubilization of the cell bound enzyme can be obtained in the presence of ionic detergents, such as sodium cholate or sodium dodecylsulfate (0.25% to 2.5%) or salts solutions, such as $Mg^{++}$ solution. The enzyme can also be precipitated by ammonium sulfate in the range of 65-95% of saturation at a temperature of about 0° C. A sonication technique can also be used to separate the levan sucrase enzyme and the cells, if necessary.

The levan sucrase enzyme can be formulated into compositions containing the levan sucrase enzyme usable in various industries, such as in particular food industries, pharmaceutical industries and chemical industries.

The levan sucrase enzyme is formulated according to its planned applications. Usually stabilizers and preservatives are also added to the enzyme compositions. For example enzyme can be stabilized by adding glycerol (50 volume %), ammonium sulfate (3.2 mol/l) or sodium chloride (3 mol/l) to the aqueous solution of the enzyme.

For medical applications the enzyme may be used preferably in lyophilized form.

For food applications the enzyme may be used immobilized by physical or chemical coupling of the enzyme to essentially insoluble inert carrier materials which facilitate their use in flow-through reactors. Usually the enzyme is attached to the carrier. Materials utilized for the carrier include organic and inorganic materials, such as porous granular diatomaceous earth treated with a solution of polyamine and glutaraldehyde, granular activated carbon, surface-active material such as alumina, carbon, clay, zirconia, titania, ion exchange resins, cellulose or glass, chemically activated supports like cellulose, agarose, synthetic polymers, gels of for example polyacrylamides, silica and starch, enzyme being captured within a polymer matrix. Preferably levan sucrase enzyme comprising Bacillus whole cells may be directly used in the immobilization process without isolation and purification of the enzyme.

The compositions containing the levan sucrase enzyme of the present invention can be utilized in either solid or liquid form. These compositions can be made into a final product which is either liquid solution, solid, granular, powder or a slurry.

The compositions according to the invention can be used for the production of levans from sugars containing fructosyl residues, such as sucrose, raffinose or stachyose. These sugars can be derived from raw materials, such as raw sugarbeets, purified juice from crushed or shredded sugar beets, molasses, cane sugars, beet sugars, plant sugars.

Levans obtained can be high molecular weight levans, low molecular weight levans (fructooligosaccharides) and fructosyl polymers.

The present invention is further illustrated by the following examples.

EXAMPLE 1

A seed medium used for inoculum development is prepared with the following components: calcium chloride 0.02% weight/volume, sodium titrate 0.3%, hydrolyzed starch 2.6% sold under the trademark MALTRIN 100 (GPC), cottonseed meal 4.6% sold under the trademark PHARMAMEDIA (TRADERS PRO- TEIN), sodium monohydrogen phosphate 0.21% and sodium dihydrogen phosphate 0.54%. This seed medium is sterilised at 125° C. during 30 minutes in seed flasks which are 250 ml triple baffled Erlenmeyer flasks containing 50 ml of seed medium. Then they are inoculated from a frozen glycerol culture of the strains of *B. licheniformis* NRRL B-18962.

The seed of this strain is developed on a gyratory shaker at 37° C. for 24 hours prior to its use as a source of inoculum for the production flasks.

The medium used for the production of levan sucrase enzyme is prepared with the following components: corn syrup 10.3% weight/volume sold under the trademark STALEY 200 corn syrup (A. E. STALEY), soybean flour 5.5% sold under the trademark PROMOSOY 100 (CENTRAL SOYA), yeast extract (sold by UNIVERSAL FOODS CORP) 0.32%, sodium monohydrogen phosphate 0.7% and sodium dihydrogen phosphate 0.7%.

This production medium is sterilised at 125° C. during 30 minutes in production flasks which are 250 ml triple baffled Erlenmeyer flasks containing 50 ml of production medium.

The inoculum size amount is 2% volume/volume. The inoculated production flasks are incubated on a gyratory shaker at a temperature of 37° C. for 16 to 20 hours.

An increase of the viscosity is not observed when levan is produced in fermentation broth.

The enzyme produced can be isolated easily with almost no stickiness.

The biomass from the flasks is separated from the fermentation broth by centrifugation whereupon the cells are washed with deionized-distilled water two times and homogenized.

The levan sucrase enzyme according to the invention is recovered.

Levan sucrase enzyme unit (LSU) is defined as the amount of enzyme activity required to produce one micromole of glucose per minute under conditions of the assay.

The enzyme activity was measured using sucrose as substrate. To one milliliter of an enzyme aliquot, 7.5 ml of 0.01M citrate buffer, pH 5.5 containing 60% sucrose (weight/weight) was added. Then the volume of the reaction mixture was adjusted to 10 ml using distilled water and incubated at 55° C. for one hour. After the specified time, the enzymatic reaction was terminated by heat at 95° C. for 10 minutes. The glucose content of the reaction products was determined by high performance liquid chromatographic (HPLC) analysis (Brobst, K. M., and H. D. Schobell, 1982. Starch/Starke, 34, 117-121).

The evaluation of the effect of pH on the activity of the levan sucrase enzyme was determined by carrying out the enzymatic transfructosylation reaction after incubation at 55° C. during one hour at different pH levels; i.e., 4.0, 4.5, 5.0, 5.5, 6.0, 6.5., 7.0, 7.5 and 8.0 using an appropriate phosphate buffer (0.01M). The amount of glucose formed was determined using HPLC (High Performance Liquid Chromatographic analysis). The activity was calculated.

At 55° C., maximum activity is developed at pH around 5.5–6.0.

FIG. 1 illustrates the effect of pH on the activity of the enzyme at a temperature of 55° C. In this figure the abscissae show the pH and the ordinates show the activity expressed as percent of the maximum activity developed at pH 5.5 and at 55° C. The symbol 0 represents the data for the enzyme according to the invention and for comparison purposes the symbol # represents the data taken from Japanese patent application JP-A-52-82781.

The enzyme of the present invention is more stable in the acidic pH range than the enzyme disclosed in said prior Japanese patent application.

The enzyme of the present invention exhibits at 55° C. and at pH 4.0 over 50% of its maximum activity measured at 55° C. whereas the enzyme of the prior art did not show any activity at pH 4.0 and at said temperature.

The FIG. 1 shows that the levan sucrase enzyme according to the invention develops an appreciable enzymatic activity in a wide pH range in the presence of sucrose. It develops at a pH in the range of about 5.5 through about 6.3 a maximum enzymatic activity measured at 55° C. More precisely it develops, at a temperature of about 55° C. and at a pH in the range of about 4.0 through about 8.4, an enzymatic activity of at least 50% of the maximum activity measured at 55° C. It develops, at said temperature of about 55° C. and at a pH in the range of about 4.2 through about 8.0, an enzymatic activity of at least 70% of the maximum activity measured at 55° C. It develops, at said temperature and at a pH in the range of about 4.5 through about 7.8, an enzymatic activity of at least 80% of the maximum activity measured at 55° C. It develops, at about 55° C. and at a pH in the range of about 4.7 through about 7.2, an enzymatic activity of at least 90% of the maximum activity measured at 55° C.

The evaluation of the effect of temperature on the activity of levan sucrase enzyme was determined by carrying out the enzymatic reaction at pH 5.5 after incubation during one hour at different temperatures, i.e., 40° C., 50° C., 55° C., 60° C., 70° C. and 80° C.

The reaction mixture consisted of 7.5 ml of 60% (weight/volume) sucrose solution in 0.01M citrate-phosphate buffer at a pH of 5.5 and 1.0 ml of washed biomass containing 30 LSU/ml enzyme activity.

At pH 5.5 maximum activity is developed at a temperature of about 60° C.

Figure 2:
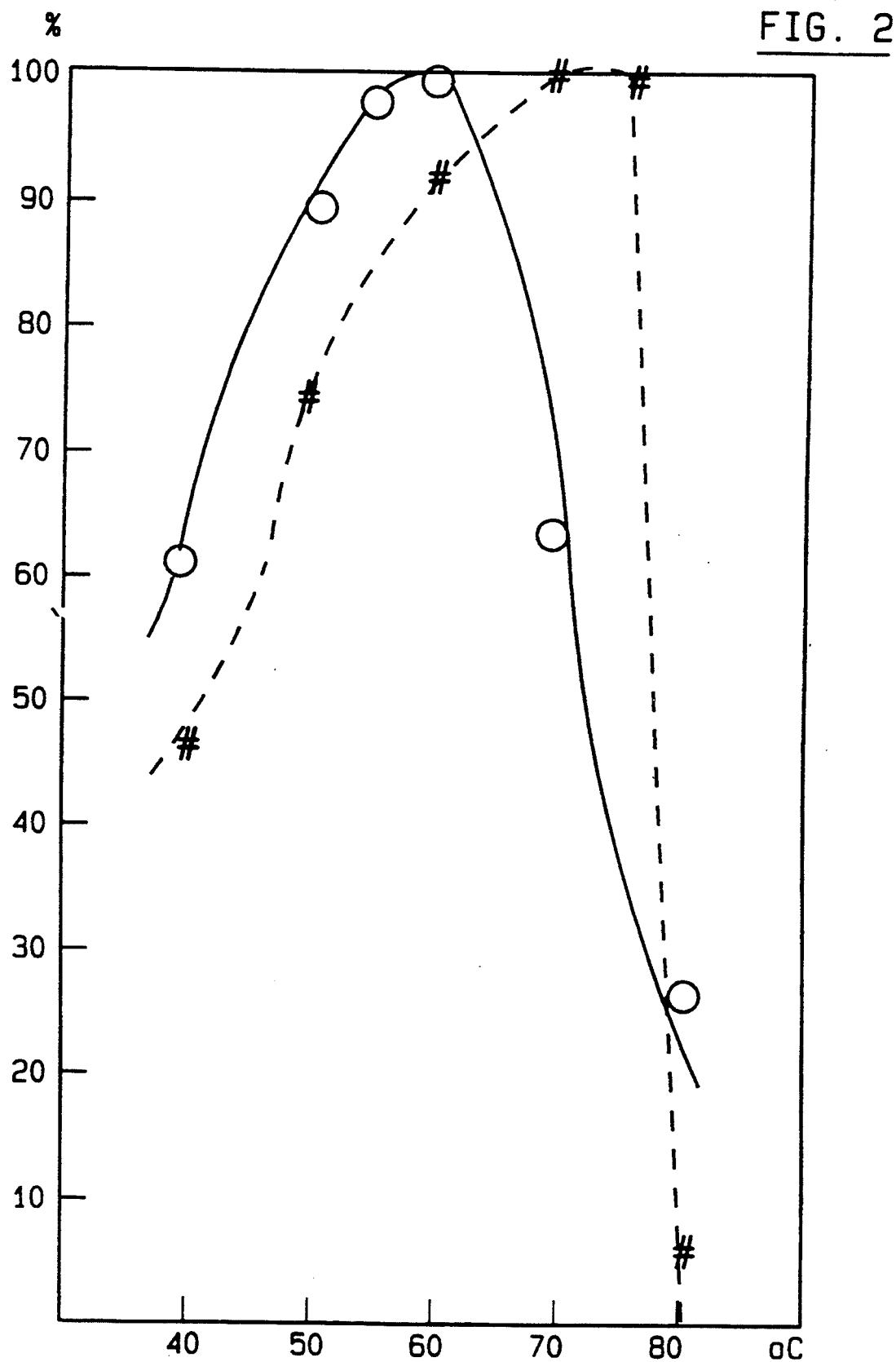

The effect of temperature on levan sucrase enzyme activity is shown in FIG. 2. In this figure the abscissae show the reaction temperature in ° C. and the ordinates show the activity expressed as percent of the maximum activity developed at 60° C. and at pH 5.5. The symbol 0 represents the data for the enzyme according to the invention and for comparison purposes the symbol # represents the data taken Japanese patent application JP-A-52-82781.

The FIG. 2 shows that the levan sucrase enzyme according to the invention has an appreciable thermal stability in the presence of sucrose.

It develops at a temperature in the range of about 55° C. through about 64° C. a maximum enzymatic activity measured at a pH of about 5.5.

More precisely it develops, at a pH of about 5.5 and at a temperature in the range of about 35° C. through about 75° C., an enzymatic activity of at least 50% of the maximum activity measured at a pH of 5.5. It develops, at said pH of about 5.5 and at a temperature in the range of about 45° C. through about 68° C., an enzymatic activity of at least 80% of the maximum activity measured at a pH of 5.5. It develops at said pH of about 5.5 and at a temperature in the range of about 50° C.

through about 67° C., an enzymatic activity of at least 90% of the maximum activity measured at a pH of 5.5.

EXAMPLE 2

The effect of levan sucrase enzyme concentration (LSU/g sucrose) on the composition of the reaction products at different time intervals was measured at a temperature of 55° C. at a pH of 5.5.

In a typical experiment, 4.5 g of sucrose in 9.5 ml of water was incubated with 0.5 ml aliquot of biomass containing different amounts of levan sucrase enzyme, i.e., 4.5, 9.0 and 22.5 LSU at a temperature of 50° C. Samples were withdrawn at different intervals of time and the reaction was terminated by heating at 90° C. for 10 minutes.

The product's composition was determined by high performance liquid chromatography (Table 1).

TABLE 1

Effect of levan sucrase enzyme concentration (LSU/g sucrose) on the composition of the reaction products

| Enzyme Concentration LSU/g Sucrose | Time [hr.] | Composition of the reaction products % | | | |
|---|---|---|---|---|---|
| | | Fructose | Glucose | Sucrose | Levan |
| 1 LSU/g | 2 | 2.48 | 4.93 | 86.82 | 5.77 |
| | 4 | 4.13 | 9.63 | 76.24 | 10.00 |
| | 6 | 5.50 | 41.06 | 66.74 | 13.70 |
| | 8 | 6.94 | 18.41 | 58.54 | 16.56 |
| | 12 | 7.49 | 23.60 | 47.30 | 21.61 |
| | 16 | 8.60 | 28.95 | 37.90 | 24.55 |
| | 24 | 9.79 | 36.35 | 23.14 | 30.71 |
| | 36 | 10.90 | 41.57 | 13.40 | 34.14 |
| | 44 | 11.24 | 42.91 | 10.55 | 35.29 |
| 2 LSU/g | 2 | 3.99 | 10.10 | 76.55 | 9.36 |
| | 4 | 6.41 | 18.59 | 58.28 | 16.72 |
| | 6 | 7.87 | 26.09 | 43.09 | 22.95 |
| | 8 | 9.03 | 32.33 | 31.59 | 27.08 |
| | 12 | 10.22 | 39.27 | 17.74 | 32.77 |
| | 16 | 10.93 | 42.93 | 11.11 | 35.02 |
| | 24 | 11.76 | 45.25 | 6.90 | 36.08 |
| 5 LSU/g | 2 | 7.19 | 23.94 | 48.02 | 20.35 |
| | 4 | 9.76 | 38.61 | 19.23 | 32.39 |
| | 6 | 10.98 | 44.28 | 8.71 | 36.02 |
| | 8 | 11.41 | 45.65 | 6.48 | 36.46 |
| | 12 | 12.34 | 45.32 | 6.43 | 35.91 |
| | 16 | 13.01 | 45.46 | 6.06 | 35.47 |

[hr.] represents the unit of hour.

The rate of formation of glucose from sucrose by levan sucrase enzyme increased with increasing concentration of the enzyme. An amount of 35% levan was produced in all the cases. A amount of 45% glucose was produced in all the cases.

EXAMPLE 3

The thermal stability of the enzyme in the presence of substrate is very important for widespread commercial application of the enzyme. The effect of temperature on the composition of the reaction products was determined at temperatures of 40° C., 50° C. and 60° C. The reaction mixture consisted of 7.5 ml of 60% (weight/weight) sucrose solution in 0.01M citrate-phosphate buffer at a pH of 5.5 and 2.5 ml of enzyme solution containing 40 units LSU. Samples were withdrawn at different intervals of time and the reaction was terminated by heating at 90° C. for 10 minutes.

The products composition was determined by high performance liquid chromatography (Table 2).

TABLE 2

Effect of temperature on the composition of the reaction products

| Reaction Temperature | Time [hr.] | Composition of the Reaction Products % | | | |
|---|---|---|---|---|---|
| | | Fructose | Glucose | Sucrose | Levan |
| 50° C. | 4 | 7.50 | 23.31 | 47.33 | 21.86 |
| | 8 | 9.15 | 35.54 | 24.16 | 31.15 |
| | 14 | 11.28 | 47.30 | 7.27 | 34.15 |
| | 24 | 11.09 | 43.32 | 10.58 | 35.01 |
| 55° C. | 4 | 7.92 | 24.32 | 45.26 | 22.50 |
| | 8 | 10.63 | 35.58 | 23.39 | 30.41 |
| | 14 | 13.80 | 46.07 | 9.07 | 30.93 |
| | 24 | 14.43 | 46.77 | 6.20 | 32.61 |
| 60° C. | 4 | 8.65 | 23.66 | 46.35 | 21.34 |
| | 8 | 11.51 | 32.14 | 29.98 | 26.36 |
| | 14 | 15.11 | 42.87 | 18.09 | 23.93 |
| | 24 | 14.55 | 40.36 | 14.74 | 30.36 |

The data in Table 2 demonstrates that the enzyme of the present invention has good thermal stability in the presence of a substrate between 50 and 65° C. at a pH of 5.5.

EXAMPLE 4

High substrate concentration is always preferred for commercial success of any transformation because of the high cost of the energy in the evaporation of reaction products.

The effect of sucrose concentration on the composition of the reaction products was studied at different intervals during incubation of sucrose at a temperature of 55° C. with the enzyme at a pH of 5.5.

Acetate buffer (0.1 M) at a pH of 5.5 containing different amounts of sucrose was prepared. Appropriate amounts of enzyme were added to a final concentration of 10 LSU/g sucrose and incubated at 55° C.

Samples were withdrawn at different intervals of time and the enzymatic reaction terminated by heating at 90° C. for 10 minutes.

The composition of the reaction products was then determined by HPLC (Table 3).

TABLE 3

Effect of sucrose concentrations on the composition of the reaction products

| Sucrose Concentration g/100 ml | Time [hr.] | % Composition | | | | Ratio of Levan to Free Fructose |
|---|---|---|---|---|---|---|
| | | Fructose | Glucose | Sucrose | Levan | |
| 30 | 5 | 9.75 | 25.69 | 43.88 | 21.57 | 2.21 |
| | 8 | 12.47 | 32.78 | 30.09 | 24.67 | 1.98 |
| | 12 | 16.14 | 43.04 | 17.75 | 23.08 | 1.43 |
| | 24 | 17.67 | 45.35 | 6.66 | 30.33 | 1.73 |
| 45 | 5 | 8.99 | 29.44 | 36.84 | 24.72 | 2.75 |
| | 8 | 10.71 | 36.40 | 22.75 | 30.13 | 2.81 |
| | 12 | 13.66 | 44.31 | 11.03 | 31.00 | 2.27 |
| | 24 | 13.56 | 42.75 | 10.20 | 33.46 | 2.46 |
| 60 | 5 | 6.93 | 29.47 | 34.12 | 29.49 | 4.26 |
| | 8 | 8.46 | 39.93 | 20.55 | 34.05 | 4.02 |
| | 12 | 11.12 | 44.98 | 8.78 | 34.12 | 3.16 |
| | 24 | 14.03 | 44.98 | 5.37 | 35.62 | 2.54 |

TABLE 3-continued

Effect of sucrose concentrations on the composition of the reaction products

| Sucrose Concentration g/100 ml | Time [hr.] | % Composition | | | | Ratio of Levan to Free Fructose |
|---|---|---|---|---|---|---|
| | | Fructose | Glucose | Sucrose | Levan | |
| 75 | 5 | 6.25 | 29.15 | 33.34 | 31.27 | 5.00 |
| | 8 | 7.57 | 37.30 | 19.00 | 36.12 | 4.77 |
| | 12 | 9.45 | 44.26 | 8.93 | 37.34 | 3.95 |
| | 24 | 10.76 | 43.31 | 4.96 | 41.12 | 3.82 |

The results set out in Table 3 show that the transfructosylation was increased with increasing concentration of sucrose. The ratio of levan produced to the free fructose at any time interval was higher at higher concentration of substrate compared to the ratio at lower concentration of the substrate. For example, the ratio of levan to free fructose lies between 1.4 to 2.2–30% sucrose concentration, whereas the ratio is 4.5–5.0 at 75% sucrose concentration. This strongly suggests that the low water activity favors the levan production.

We claim:

1. A levan sucrase enzyme produced by *Bacillus licheniformis* APMC 84 having deposit number NRRL B-18962 and mutants thereof capable of producing said levan sucrase enzyme wherein said enzyme possesses at a temperature of about 55 C. a maximum activity at a pH of about 5.5 and retains at least 50% of its maximum activity at a pH of 4.0, as determined by the amount of glucose produced under the assay conditions which include sucrose as a substrate and measurement by high performance liquid chromatography.

2. The levan sucrase enzyme of claim 1 wherein said enzyme is produced in the absence of sucrose.

3. The levan sucrase enzyme according to claim 1 wherein at a temperature of about 55 C. said enzyme possesses a maximum activity at a pH in the range of about 5.5 through about 6.3.

4. The levan sucrase enzyme according to claim 1 or 2 wherein said enzyme retains at least 50% of its maximum activity at a temperature of about 55° C. and at a pH in the range of about 4.0 through about 8.4.

5. The levan sucrase enzyme according to claim 4, wherein said enzyme retains at least 80% of its maximum activity at a temperature of about 55° C. and at a pH in the range of about 4.5 through about 7.8.

6. The levan sucrase enzyme according to claim 1 or 2, wherein said enzyme possesses a maximum activity at a temperature of about 55 C. and a pH of about 5.5 and retains at least 50% of its maximum activity at a temperature range of about 35 C. through about 75 C.

7. A liquid solution comprising the levan sucrase enzyme according to claim 1 in combination with a suitable carrier.

8. The liquid solution according to claim 7, further comprising a stabilizer.

9. The levan sucrase enzyme according to claim 1, wherein said enzyme is lyophilized.

10. The levan sucrase enzyme according to claim 1, wherein said enzyme is coupled to an essentially insoluble inert carrier, so as to be immobilized.

11. A levan sucrase enzyme produced by *Bacillus licheniformis* APMC 84, having deposit number NRRL B-18962, and mutants thereof capable of producing said levan sucrase enzyme, wherein said enzyme possesses at a temperature of about 55 C. a maximum activity at a pH of about 5.5 and retains at least 50% of its maximum activity at a pH of 4.0, as determined by the amount of glucose produced under assay conditions which include sucrose as a substrate and measurement by high performance liquid chromatography, and wherein said levan sucrase enzyme is produced by a process comprising the steps of:
(i) cultivating *Bacillus licheniformis* APMC 84 or mutants thereof in a suitable nutrient medium by forming a fermentation broth comprising a biomass; and
(ii) recovering the levan sucrase enzyme from said fermentation broth,
and wherein said *Bacillus licheniformis* APMC 84 or mutants thereof is cultivated in the absence of sucrose.

* * * * *